United States Patent [19]

Chick et al.

[11] Patent Number: 5,342,789
[45] Date of Patent: Aug. 30, 1994

[54] METHOD AND DEVICE FOR DETECTING AND QUANTIFYING GLUCOSE IN BODY FLUIDS

[75] Inventors: William L. Chick, Wellesley; David E. Wolf, Hudson; Richard A. Cardullo, Milford, all of Mass.

[73] Assignee: Sensor Technologies, Inc., Hingham, Mass.

[21] Appl. No.: 452,122

[22] Filed: Dec. 14, 1989

[51] Int. Cl.$^5$ ............... G01N 33/566; G01N 33/542; A61B 5/00; A61K 49/00

[52] U.S. Cl. ...................... 436/501; 436/95; 436/537; 436/805; 436/807; 436/815; 128/632; 128/633; 128/634; 424/9

[58] Field of Search ............... 436/501, 95, 537, 805, 436/807, 815; 128/634; 604/632, 633, 634; 424/9

[56] References Cited

U.S. PATENT DOCUMENTS

| | | | |
|---|---|---|---|
| 4,330,299 | 5/1982 | Cerami | 23/230 |
| 4,344,438 | 8/1982 | Schultz | 128/634 |
| 4,401,122 | 8/1983 | Clark, Jr. | 128/635 |
| 4,981,779 | 1/1991 | Wagner | 435/288 |
| 5,028,787 | 7/1991 | Rosenthal et al. | 250/341 |
| 5,143,066 | 9/1992 | Komives et al. | 128/634 |

OTHER PUBLICATIONS

Meadows, et al., "Fiber-optic Biosensors Based on Fluorescence Energy Transfer", *Talanta*, vol. 35, No. 2, pp. 145–150, 1988.
Cardullo, et al. PNAS 85: 8790–8794 (1988).
Schultz et al., Diabetes Care 5 (3): 245–253 (1982).
Heller et al., "Chemiluminescent and Fluorescent Probes for DNA Hybridization Systems" pp. 245–257 (1985).
Wilson, *Biotechnology*, pp. 3–4 (1983).
Morrison, *Gene Probe Technology II* (1987), paper No. 6.
Heller, et al., *Federation Proceedings* 46 (6) (1987), abstract No. 248.
Parker et al., *Proc. SPIE-Int. Soc. Opt. Eng.*, 713:113–20 (1987).

*Primary Examiner*—Margaret Parr
*Assistant Examiner*—Bradley L. Sisson
*Attorney, Agent, or Firm*—Fish & Richardson

[57] ABSTRACT

A method for quantifying glucose concentration in blood, body fluids, and other samples within, below and above the normal physiological range, which relies on non-radiative fluorescence resonance energy transfer, as well as devices useful in quantifying blood glucose concentration using the present method.

28 Claims, 7 Drawing Sheets

D  DONOR
A  ACCEPTOR
M  MACROMOLECULE
L  LECTRIN
G  GLUCOSE

1) NO ENERGY TRANSFER
2) COMPLETE ENERGY TRANSFER
3) PARTIAL ENERGY TRANSFER DUE TO GLUCOSE COMPETITION

1) NO ENERGY TRANSFER
2) COMPLETE ENERGY TRANSFER
3) PARTIAL ENERGY TRANSFER DUE TO GLUCOSE COMPETITION

METHOD AND DEVICE FOR DETECTING AND QUANTIFYING GLUCOSE IN BODY FLUIDS

BACKGROUND OF THE INVENTION

Determination of glucose concentration has applications in clinical settings, such as for the day-to-day monitoring of glucose levels in individuals in whom glucose homeostasis is not maintained (e.g., in diabetes or hypoglycemia) and in biomedical research.

Current methods for determining glucose concentrations include various colorimetric reactions, measuring a spectrophotometric change in the property of any number of products in a glycolytic cascade or measuring the oxidation of glucose using a polarographic glucose sensor. For example, U.S. Pat. No. 4,401,122 discloses an in vivo method for measuring glucose, which involves placing an enzyme (e.g., glucose oxidase) either in or under the skin and detecting the enzymatic reaction product (e.g., oxygen) directly through the skin using polarographic or enzyme electrodes. The amount of enzymatic reaction product detected is a measure of the amount of substrate.

Although conventional assays have proven reliable, the reagents on which they rely become exhausted in the presence of glucose. Therefore, these assays require the use of disposable sticks or replaceable cartridges, which can be expensive and inconvenient for the active user.

Meadows and Schultz describe another method by which blood glucose levels can be determined using optical means. They describe a fiber optic glucose sensor based on the competitive binding of glucose and fluorescein-labelled dextran (FITC-dextran) to rhodamine-labelled concanavalin A (Rh-Con A), Meadows, D. and J. S. Schultz, *Talanta*, 35:145–150 (1988).

The Meadows and Schultz optical sensor is attended by many problems, which means it is of limited use in a clinical setting or in monitoring blood glucose levels in individuals on a day to day basis. First, as mentioned in the article, the sensor can only detect glucose concentrations up to 2.00 mgs/ml. Although the normal physiologic blood glucose concentration in man is approximately 1.00 mg/ml., the concentration of glucose in diabetic blood can often exceed 3.00–4.00 mg/ml., which is well beyond the upper limit of the sensor described.

Second, Meadow's and Schultz's sensor has a short life because, as mentioned in the article, the dextran aggregates and becomes precipitated. Third, only 45% of the fluorescence is quenched using the Meadows and Schultz optical sensor. This effect may not be dramatic enough to be detected.

Finally, the in vivo use of a fiber optic is clinically impractical because in order to work, it must pierce the skin. Therefore, it requires an invasive technique and puts the patient at significant risk for developing serious infection. This is particularly true in diabetic patients who are known to have reduced resistance to infection.

An ideal glucose sensor should be capable of detecting a wide range of glucose concentrations (e.g., concentrations ranging from 0.5 to 5.00 mg/ml.). It should also be reliable, reusable and easy to use. In addition, an in vivo sensor should be non-invasive. Such a sensor would be of great value in markedly improving therapy in diabetic patients. It would also have a number of other research and clinical applications.

SUMMARY OF THE INVENTION

The present invention relates to a method of detecting and quantifying glucose in a body fluid using non-radiative fluorescence resonance energy transfer (FRET) and devices useful in carrying out the present method of glucose detection and measurement.

In the method of the present invention, the body fluid is contacted with a specific binding pair, the two members of which are a labelled ligand and a labelled carbohydrate-containing receptor (referred to as a labelled glycoconjugate) which binds specifically to the ligand in competition with glucose. Each member of the binding pair is labelled with a light-absorbing material. In general, two light-absorbing materials with overlapping excited state energy levels are used, one affixed to the ligand and one to the glycoconjugate.

In particular, in the method of the present invention, two fluorescently-labelled substances, a ligand (e.g., lectin, monoclonal antibody) and a carbohydrate-containing receptor or glycoconjugate which binds specifically to the ligand in competition with glucose are brought into contact with the body fluid, either within the body or as a sample obtained using known methods. Each member of the specific binding pair is labelled with a fluorophore; generally, they are labelled with two different fluorophores. For the purposes of FRET, the ligand can be labelled with either a donor or an acceptor molecule. If the ligand is labelled with a donor, the glycoconjugate is generally labelled with an acceptor. If the ligand is labelled with an acceptor, the glycoconjugate is generally labelled with a donor.

FRET occurs only when the donor and acceptor are in sufficiently close proximity to one another (generally, within 100 angstroms). In the method of the present invention, FRET results when the ligand and glycoconjugate in the sample bind. However, in the presence of glucose, these molecules are competed off (i.e., glucose competes with the glycoconjugate in binding with the ligand). Thus, the presence and concentration of glucose in a sample are indicated as a decrease in the efficiency of energy transfer. Competition with glucose occurs in a dose-dependent manner and is reversible. In addition, because the glycoconjugates are stable, the devices of the invention can be reused for extended periods of time.

The method of the present invention makes use of the fact that when two light-absorbing materials with overlapping excited state energy levels are in sufficiently close proximity, a resonance dipole-induced dipole interaction occurs and, as a result, the excited state energy of the donor molecule is transferred to the acceptor molecule, resulting in quenching of the donor fluorescence and sensitized emission of the acceptor.

Such materials, which are attached to or incorporated in members of the specific binding pairs (i.e., the ligands and the glycoconjugates) used in the method of the present invention, can be, for example, fluorescent materials, such as fluorescein and rhodamine. Alternatively, one (the donor) can be fluorescent in nature and the other (the acceptor) nonfluorescent. The reverse is also possible (i.e., nonfluorescent donor, fluorescent acceptor).

A number of devices can be constructed and used to detect glucose concentration in blood or other samples (e.g., urine or extracellular fluid), either in vivo or in vitro, using the method of the present invention. In its broader aspect, the in vivo embodiment of this invention is directed to measurement of glucose by placing reactants (e.g., fluorescently-labelled ligand and glycoconjugate labelled with a second fluorophore) in communication with (e.g., contacting) glucose present in a body fluid. For example, the reactants can be placed in, on, or under the skin, and cutaneous measurement of glucose carried out. Alternatively, the two reactants can be introduced into an organ or vessel in which communication of glucose with the reactants is possible. In the embodiment in which reactants are placed in, on or under the skin, glucose is detected and quantified by illuminating the skin (e.g., at the excitation wavelength of the donor). The measure of energy transfer, as detected by a fluorimeter, is then either the ratio of fluorescence intensities at the two emission maximum wavelengths or the quenching of the donor fluorescence at its emission maximum as a function of glucose concentration.

A variety of modes of placing the reactants in communication with glucose may be employed in accordance with the principles of the in vivo embodiment of this invention. In addition, any mode of placing the reactants in communication with glucose can be modified to provide feedback for an insulin pump.

In its broader aspect, the in vitro embodiment of this invention is directed to placing the reactants in communication with a sample of body fluid containing glucose (e.g., blood, urine, extracellular fluid), such as by contacting the fluid with a dipstick on which the reactants are affixed. Glucose is detected and quantified by placing the reactants in communication with the glucose-containing body fluid in a fluorimeter. As with the in vivo embodiment, a variety of modes of placing the reactants in communication with glucose may be employed.

The method and devices of the present invention can be used to detect a wide range of glucose concentrations (e.g., concentrations ranging from 0.5 to 18 mg/ml.). In addition, the method is reliable, because the reactants do not interfere with the determination by aggregating and the size of the effect, as measured by the ratio of fluorescence intensities at the emission maximum wavelengths of the donor and/or acceptor or the quenching of the donor at its emission maximum as a function of glucose, is large enough that it is easily detected.

Also, because the reactants are not consumed, the devices are reusable for extended periods. Finally, the in vivo embodiments are completely non-invasive or are non-invasive after one implant.

DETAILED DESCRIPTION OF THE INVENTION

The present invention relates to a method of detecting and quantifying glucose in a body fluid and to devices useful in carrying out the present method of glucose detection and measurement. The present method relies on the process of non-radiative fluorescence resonance energy transfer (FRET) to determine the occurrence and extent of binding between members of a specific binding pair which is competitively decreased by glucose. Members of the binding pair are a ligand (e.g., a lectin, monoclonal antibody) and a carbohydrate-containing receptor (referred to as a glycoconjugate), which binds specifically to the ligand in competition with glucose. Both the ligand and the glycoconjugate are fluorescently labelled, but typically are not labelled with the same fluorophore. They are brought into contact with a sample (e.g., blood, urine, extracellular fluid) in which glucose concentration is to be determined.

The present method is particularly useful in the day-to-day monitoring of glucose concentrations in individuals in whom glucose homeostasis is compromised (e.g., diabetic or hypoglycemic individuals) and in biomedical research.

Basic Elements of FRET

FRET generally involves the non-radiative transfer of energy between two fluorophores, one an energy donor (D) and the other an energy acceptor (A). Any appropriately selected donor-acceptor pair can be used, provided that the emission of the donor overlaps with the excitation spectra of the acceptor and both members can absorb light energy at one wavelength and emit light energy of a different wavelength.

The method is described below with particular reference to fluorescein and rhodamine as the donor-acceptor pair. As used herein, the term fluorescein refers to a class of compounds which includes a variety of related compounds and their derivatives. Similarly, as used herein, the term rhodamine refers to a class of compounds which includes a variety of related compounds and their derivatives. Other examples of donor/acceptor pairs are NBD N-(7-mitrobenz-2-oxa-1,3-diazol-4-yl) to rhodamine, NBD or fluorescein to eosin or erythrosis, dansyl to rhodamine, acridine orange to rhodamine.

Alternatively, one molecule (the donor) can be fluorescent and the other (the acceptor) can be nonfluorescent. It is also possible to make use of a donor-acceptor pair in which the acceptor is not normally excited at the wavelength used to excite the (fluorescent) donor; however, nonradiative FRET causes acceptor excitation.

Although the donor and the acceptor are referred to herein as a "pair", the two "members" of the pair can, in fact, be the same substance. Generally, the two members will be different (e.g., fluorescein and rhodamine). It is possible for one molecule (e.g., fluorescein, rhodamine) to serve as both donor and acceptor; in this case, energy transfer is determined by measuring depolarization of fluorescence.

Figure 1A:
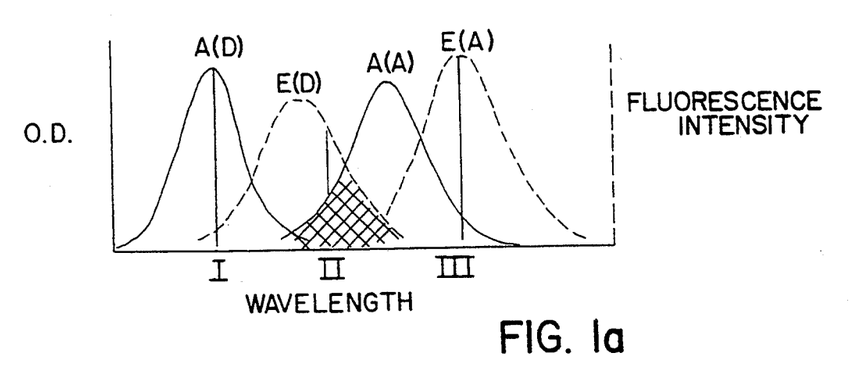
FIG. 1A is a graphic representation of absorbance and emission spectra of donor and acceptor molecules.

The concept of FRET is represented in FIG. 1. The absorbance and emission of donor, designated A(D), and E(D), respectively, and the absorbance and emission of acceptor, designated A(A) and E(A), respectively, are represented graphically in FIG. 1A. The area of overlap between the donor emission and the acceptor absorbance spectra (which is the overlap integral) is of importance. If excitation occurs at wavelength I, light will be emitted at wavelength II by the donor, but not at wavelength III by the acceptor because the acceptor does not absorb light at wavelength I.

Figure 1B:
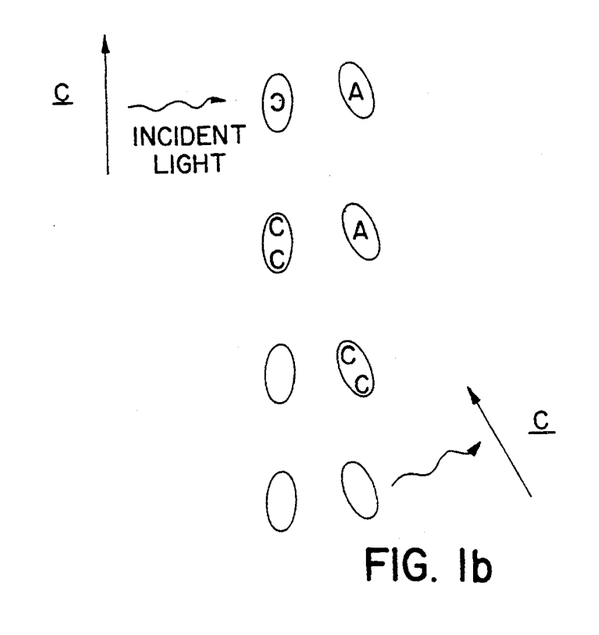
FIG. 1B is a representation of non-radiative energy transfer.

The non-radiative transfer process which occurs is represented in FIG. 1B. D molecule absorbs the photon whose electric field vector is represented by E. The excited state of D is shown as a dipole with positive charge on one side and negative charge on the other. If an acceptor molecule (A) is sufficiently close to D (e.g., typically less than 100 Angstroms), an oppositely charged dipole is induced on it (it is raised to an excited state). This dipole-induced dipole interaction falls off inversely as the sixth power of donor-acceptor intermolecular distance.

Classically, partial energy transfer can occur. However, this is not what occurs in FRET, which is an all or nothing quantum mechanical event. That is, a donor is not able to give part of its energy to an acceptor. All of the energy must be transferred and energy transfer can occur only if the energy levels (i.e., the spectra) overlap. When A leaves its excited state, the emitted light is rotated or depolarized with respect to the incident light. As a result, FRET manifests itself as a decrease in fluorescence intensity (i.e., decrease in donor emission) at II, an appearance of fluorescence intensity at III (i.e., an increase in sensitized emission) and a depolarization of the fluorescence relative to the incident light.

A final manifestation of FRET is in the excited state lifetime. Fluorescence can be seen as an equilibrium process, in which the length of time a molecule remains in its excited state is a result of competition between the rate at which it is being driven into this state by the incident light and the sum of the rates driving it out of this state (fluorescence and non-radiative processes). If a further nonradiative process, FRET, is added (leaving all else unchanged), decay is favored, which means donor lifetime at II is shortened.

When two fluorophores whose excitation and emission spectra overlap are in sufficiently close proximity, the excited state energy of the donor molecule is transferred by a resonance dipole-induced dipole interaction to the neighboring acceptor fluorophore. In FRET, a sample or mixture is illuminated at a wavelength which excites the donor but not the acceptor molecule directly. The sample is then monitored at two wavelengths: that of donor emissions and that of acceptor emissions. If donor and acceptor are not in sufficiently close proximity, FRET does not occur and emissions occur only at the donor wavelength. If donor and acceptor are in sufficiently close proximity, FRET occurs. The results of this interaction are a decrease in donor lifetime, a quenching of donor fluorescence, an enhancement of acceptor fluorescence intensity, and depolarization of fluorescence intensity. The efficiency of energy transfer, $E_t$, falls off rapidly as the distance between donor and acceptor molecule, R, increases. For an isolated donor acceptor pair, the efficiency of energy transfer is expressed as:

$$E_t = 1/[1+(R/R_o)^6] \quad (1)$$

where R is the separation distance between donor and acceptor and $R_o$ is the distance for half transfer. $R_o$ is a value that depends upon the overlap integral of the donor emission spectrum and the acceptor excitation spectrum, the index of refraction, the quantum yield of the donor, and the orientation of the donor emission and the acceptor absorbance moments. Forster, T., *Z Naturforsch.* 4A, 321–327 (1949); Forster, T., *Disc. Faraday Soc.* 27, 7–17 (1959).

Because of its $1/R^6$ dependence, FRET is extremely dependent on molecular distances and has been dubbed "the spectroscopic ruler". (Stryer, L., and Haugland, R. P., *Proc. Natl. Acad. Sci. USA*, 98:719 (1967). For example, the technique has been useful in determining the distances between donors and acceptors for both intrinsic and extrinsic fluorophores in a variety of polymers including proteins and nucleic acids. Cardullo et al. demonstrated that the hybridization of two oligodeoxynucleotides could be monitored using FRET (Cardullo, R., et al., *Proc. Natl. Acad. Sci.*, 85:8790–8794 (1988)).

Concept of Using FRET to Measure Glucose Concentrations

Figure 2:
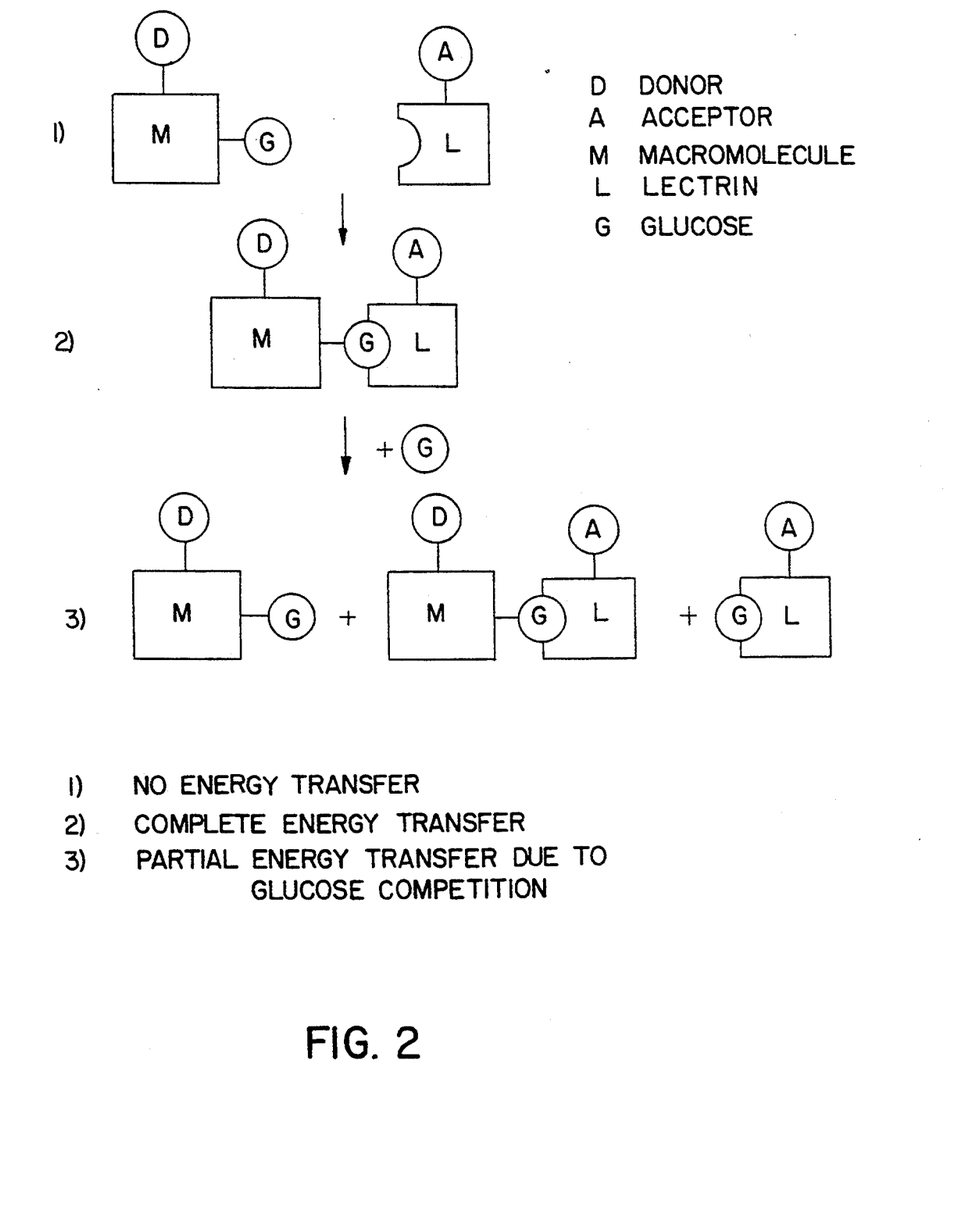
FIG. 2 is a graphic representation of the use of FRET to measure glucose concentrations in a sample.

The concept of using FRET to measure glucose concentrations in solution is represented in FIG. 2. One macromolecule (designated M) includes a number of covalently-bound fluorophores and glucose residues and is referred to as a glycoconjugate. A second macromolecule (designated L) includes a ligand which has a high degree of specificity for glucose (e.g., concanavalin A) and a fluorophore which is generally not the same fluorophore as that on the first macromolecule.

One of these fluorophores is chosen to be a donor and the other is an acceptor as described previously. For the purposes of this illustration, the donor molecule has been placed on the glycoconjugate and the acceptor has been placed on the ligand. The association can then be diagrammed as:

where DMG stands for Donor-Macromolecule-Glucose, AL stands for Acceptor-Ligand, and DMG-LA represents the association between the glucose present in the first complex and the ligand present in the second complex. Upon association, the two macromolecules are now close enough to allow energy transfer between the donor and the acceptor to occur.

The presence of free glucose introduces a competitive inhibitor into the formula because free glucose competes with the conjugated glucose for the ligand. Thus, increasing concentrations of glucose produces a decrease in the amount of ligand binding to the glycoconjugate. At relatively low concentrations of glucose, the transfer efficiency will remain high, since little of the macromolecular association will be affected. At high concentrations of glucose, the transfer efficiency will be low, due to the fact that the glucose has successfully competed the ligand off of the complementary macromolecule.

As described in the following sections, it has been shown that it is possible to obtain a reliable, repeatable measure of glucose in a sample containing glucose concentrations within the range typically found in normal individuals and in those in whom glucose homeostasis is altered (e.g., in diabetic and hypoglycemic patients). Further, it has been shown that the reactants used (i.e., fluorescently-labelled ligand and glycoconjugate) are stable and can be reused.

Competition experiments in which FRET was measured for various concentrations of glucose in Hanks Buffered Salt Solution (HBSS) were conducted. These experiments are described in detail in Example 3. Spectra were collected by exciting fluorescein at 472 nm and scanning the emission from 500–650 nm. Typically, fluorescence intensities were monitored at the emission maxima for fluorescein (about 520 nm) and rhodamine (about 596 nm). The measure of energy transfer in these studies was either the ratio of fluorescence intensities at 520 nm and 596 nm (i.e., FI 520/FI 596) as a function of glucose concentration or the quenching of fluorescein at 520 nm.

Figure 3:
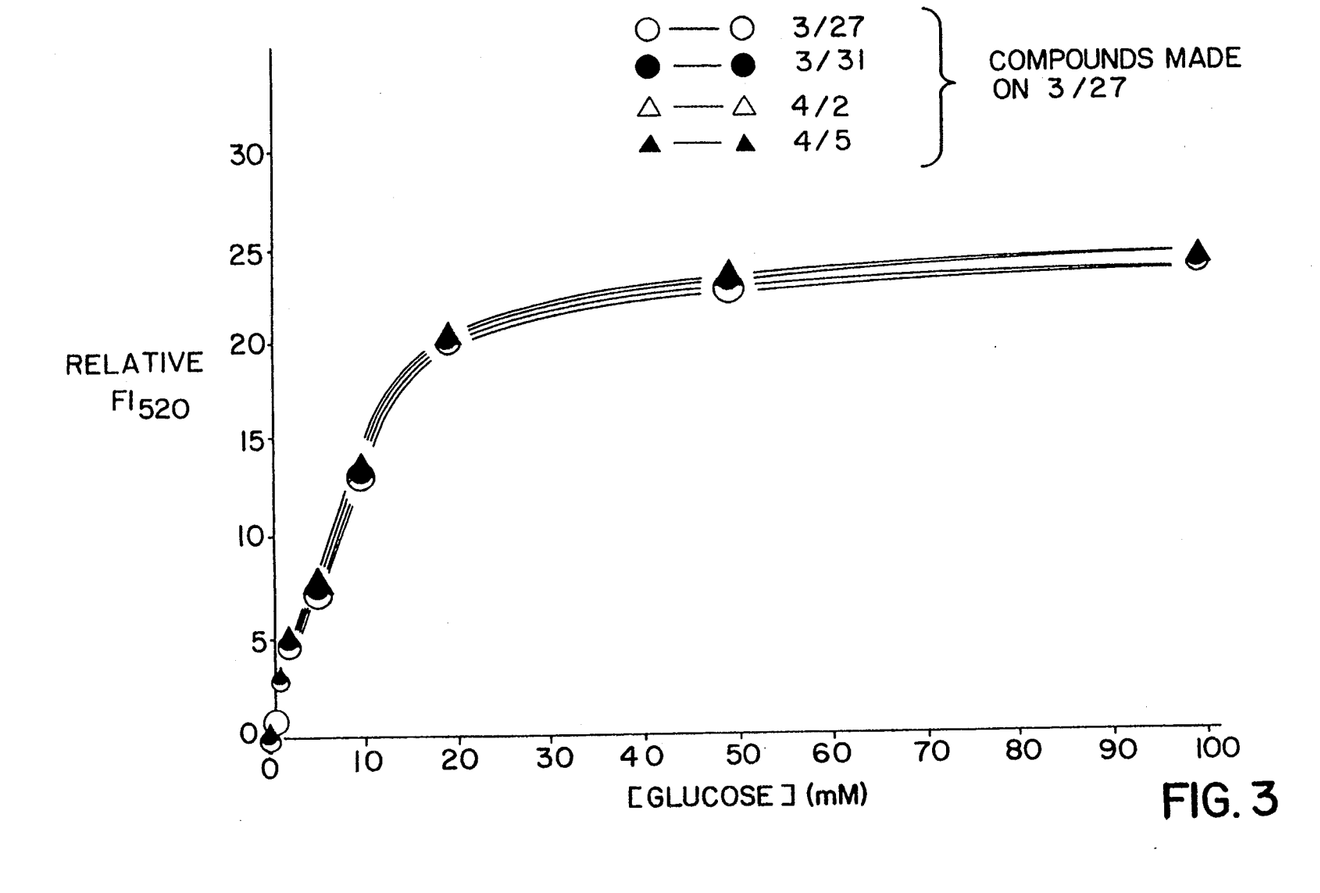
FIG. 3 is a graph representing the effect that increasing concentrations of glucose have on FRET between the fluorescently labelled ligand, Rhodamine-ConA (RC) and the fluorescently labelled glycoconjugate, fluorescein BSA-Glucose (FBG) over time.

A number of observations were made during these trials that indicate that the method of the subject invention provides a reliable means of detecting glucose over a wide range (i.e., glucose concentrations found in normal, hypoglycemic and diabetic subjects). Firstly, the compounds were found to be stable over 2–4 weeks at room temperature. FIG. 3 shows that the compounds exhibited the same fluorescence properties over a two week time period in response to glucose concentration. Data in the graph reflect the change in fluorescence intensity at 520 nm from 0 mM glucose as a function of glucose concentration.

Secondly, the glucose concentration determined by FRET is in accordance with measurements using other meters. In a double blind experiment, FRET was able to predict glucose concentrations within ±10% of those measured using a Direct 30/30 Glucometer in a range of 60–300 mg/dL.

Figure 4:
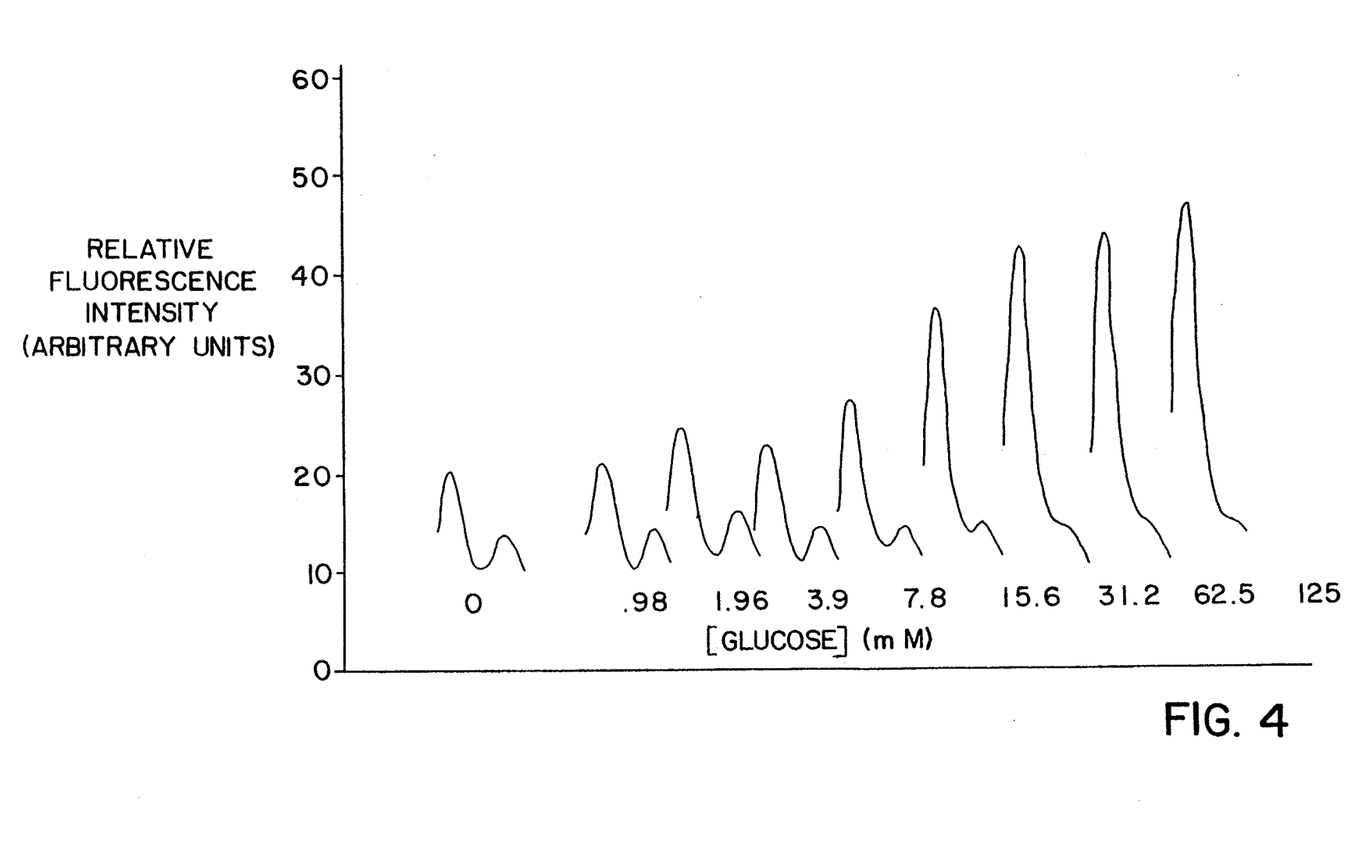
FIG. 4 is a graph representing FRET between FBG and RC dialyzed against various concentrations of glucose in Hanks Buffered Salt Solution (HBSS).

In addition, FIG. 4 shows that the FRET method was able to predict glucose concentrations accurately at concentrations up to 31 mM glucose (~600 mg/dL), which is well within and in excess of the desired range. Normal glucose concentrations in blood are usually between 80 and 120 mg/dL and diabetic levels can exceed 500 mg/dL. In the range of 0 to 31 mM glucose, the response by FRET was nearly linear with a coefficient of determination ($r^2$) of 0.983. Therefore, the sensor is reliable for detecting glucose concentrations over the entire physiologic range (i.e., for normal and hyperglycemic (diabetic) individuals.

Figure 5:
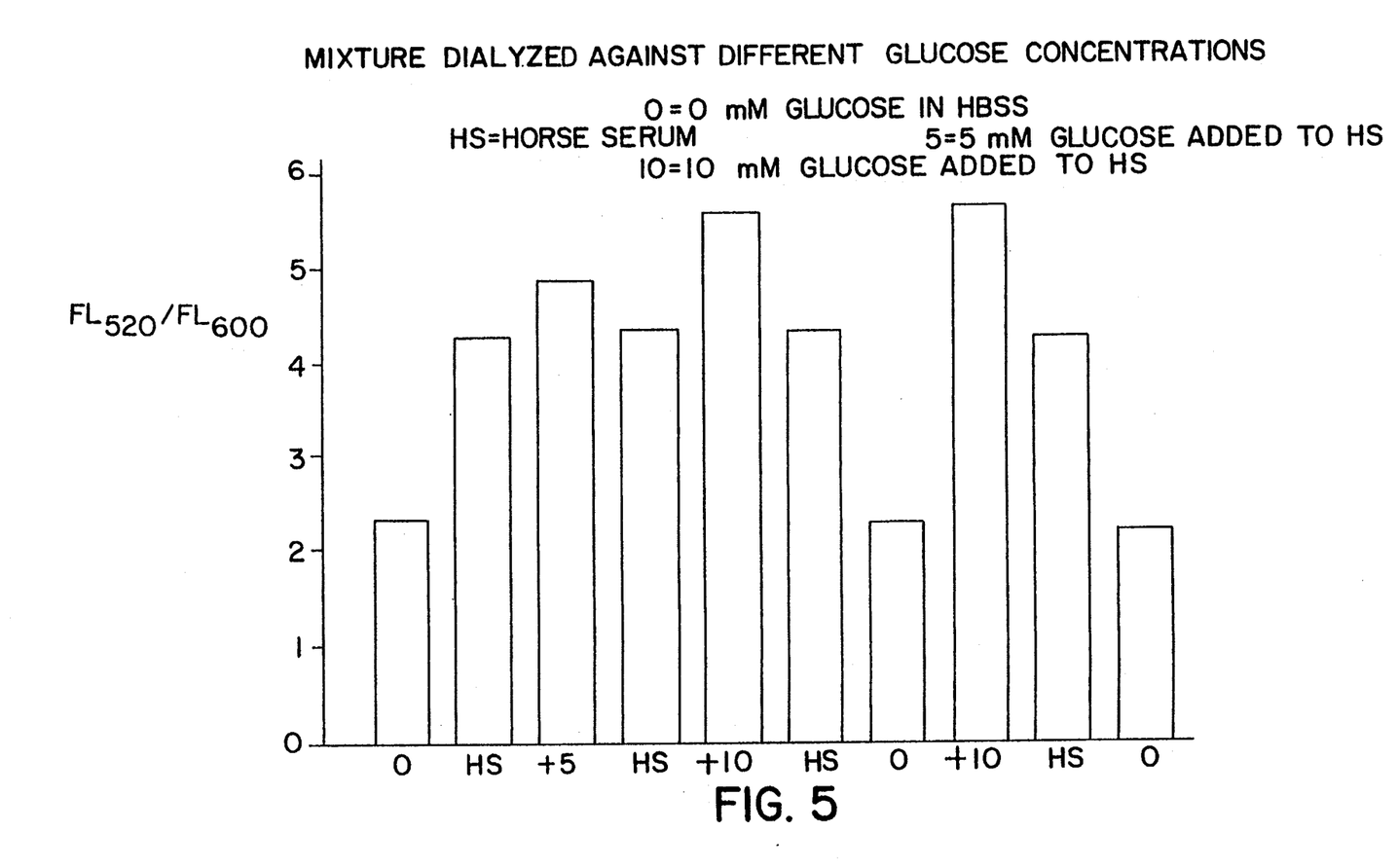
FIG. 5 is a bar graph of $Fl_{520}/Fl_{600}$ ratio for a sample of FBG and RC dialyzed sequentially against variour different glucose concentrations in the following: (reading left to right on the X axis) (O) Hanks Buffered Salt Solution; (HS) normal horse serum; (+5) horse serum +5 mM glucose; (HS) horse serum; (HO) normal horse serum +10 mM glucose; (HS) normal horse serum; (O) Hanks Balanced Salt Solution; (+10) normal horse serum +10 mM glucose; (HS) horse serum; (O) Hanks Balanced Salt Solution.

The components of the present invention were also found to be reusable. When FBG and RC were placed into 8–11 kD cutoff dialysis tubing and dialyzed against different glucose concentrations in serum, FRET accurately determined these concentrations in accordance with solution studies. The initial volume of FBG and RC in HBSS was 2 ml and dialyzed against different glucose concentrations in 50 ml volumes. In general, it took approximately 30 minutes to reach a plateau level in the $FI_{520}/FI_{600}$ ratio. As shown in FIG. 5, the response is reversible as the dialysis tubing was changed into different glucose concentrations. Experiments in horse serum showed that the response was not affected by dialyzed components, but did shift the baseline due to light scattering.

The method of the subject invention can be used to detect and quantify glucose in samples of a size appropriate for obtaining from an individual (e.g., 10–100 μl). In assessments carried out using these microsamples of normal human blood, the glucose level was found to be essentially the same as a measurement made simultaneously on a conventional glucose meter.

Figure 6A:
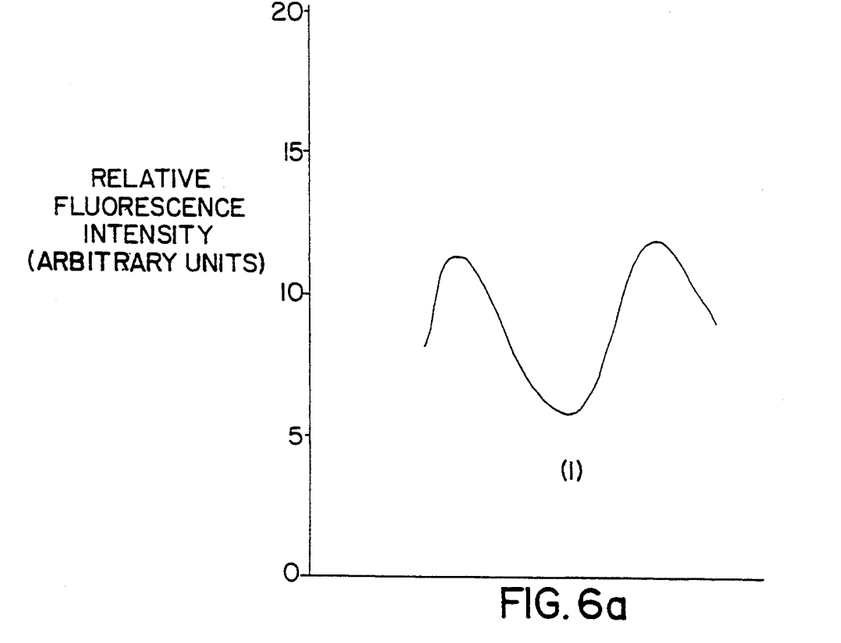
FIG. 6A is a graph representing FRET between FBG and RC with no glucose present (control).

The ability of the present method to determine the glucose concentration in hyperglycemic blood (i.e., a sample of normal blood augmented with glucose to produce glucose levels observed in diabetic individuals) was also assessed. FIG. 6 shows the raw data scans from this experiment. The first (FIG. 6A) is an emission scan from 500 nm of a sample excited at 472 nm which does not contain glucose. It shows considerable energy transfer, as evidenced by the ratio of the two emission peaks. The rhodamine (second) peak is actually higher than the fluorescein (first) peak.

Figure 6B:
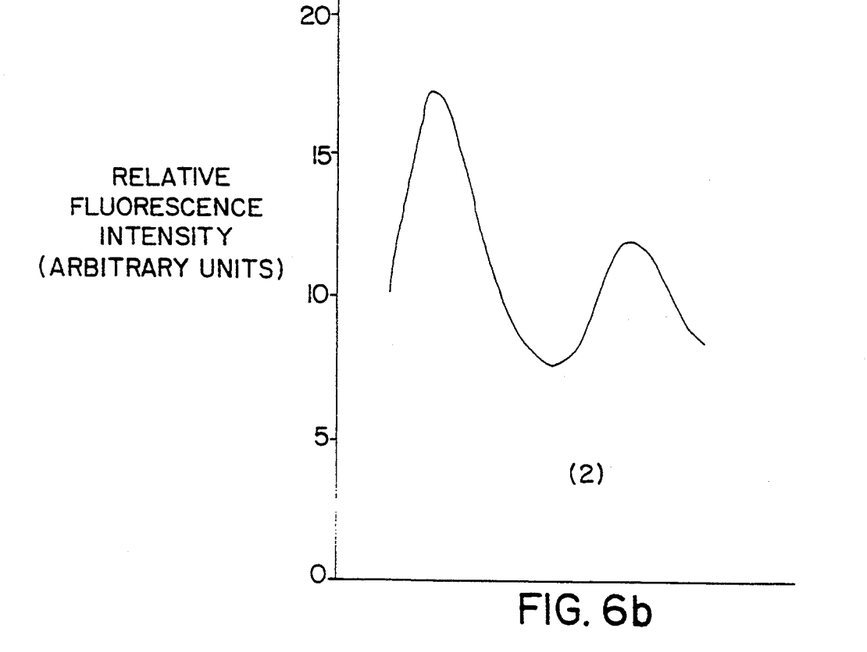
FIG. 6B is a graph representing FRET between FBG and RC microdialyzed against blood containing 3.2 mg/ml. of glucose, similar to what might be found in diabetic patients.

The second scan depicted in FIG. 6B shows the effect of dialyzing against a blood sample with hyperglycemic levels of glucose, here 317 mg/dL. The energy transfer decreases as seen both in the increase of the fluorescein emission peak and a concurrent decrease in the sensitized rhodamine emission.

Figure 7:
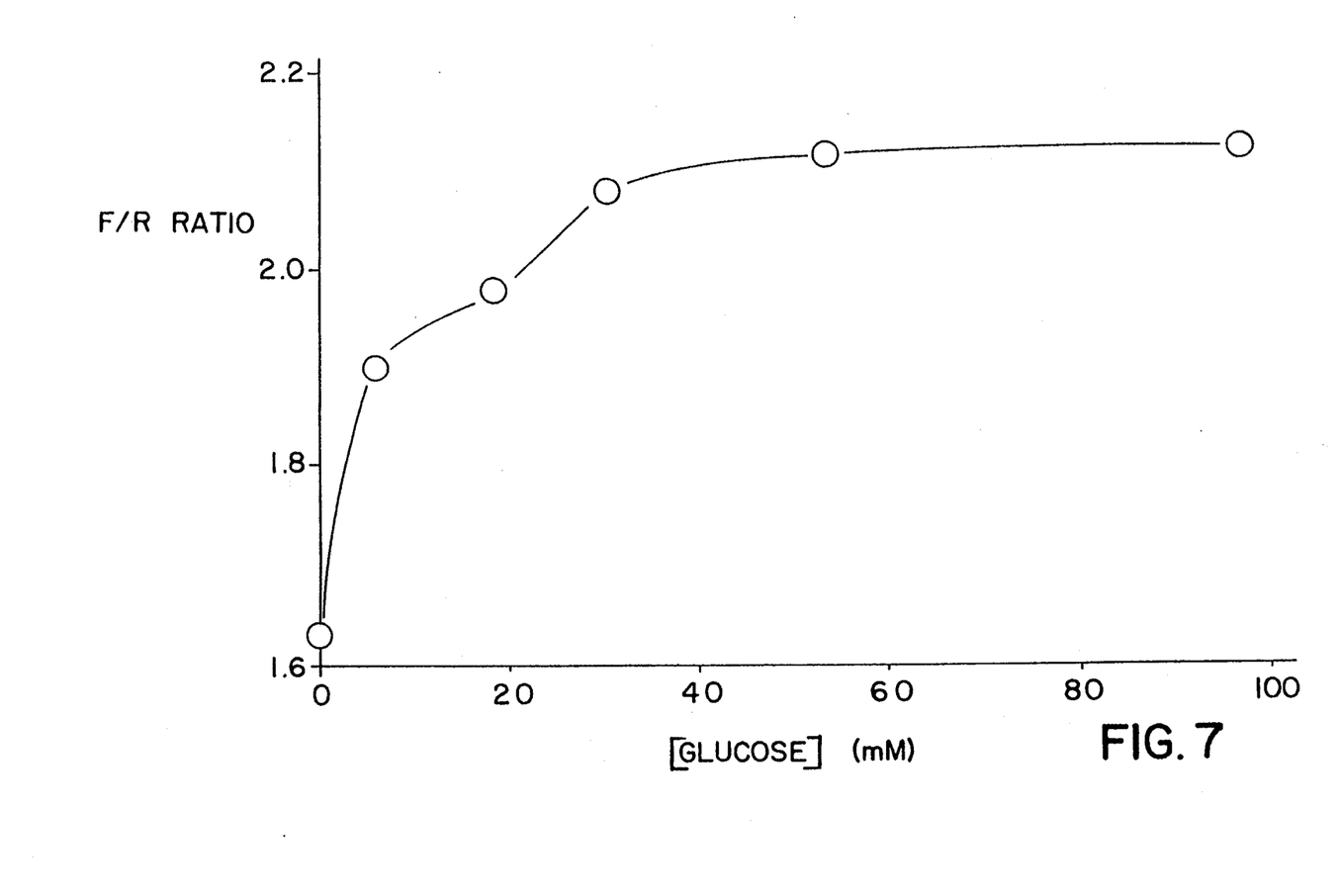
FIG. 7 is a graph representing FRET in response to 150 uls of a mixture of RC and FBG microdialyzed against blood containing varying concentrations of glucose.

The present method was shown to be effective in assessing glucose levels in blood and is sensitive in the hyperglycemic range in the following way: 150 μl of a mixture of Rh-Con A and FBG was microdialyzed for 15 minutes against 1500 μl samples of hyperglycemic blood. FIG. 7 shows that the initial fluorescein/rhodamine fluorescence ratio was just above 1.6 and that the fluorescein/rhodamine fluorescence ratio increased as a function of glucose concentration, saturating at about 40 mM glucose.

Based on the method of the subject invention a number of devices can be constructed to detect glucose concentration in blood either in vivo or in vitro. These devices can remain active for extended periods of time (e.g., one month or more) before having to be replaced.

In vivo embodiments of this invention are directed to cutaneous measurement of glucose by placing the reactants (i.e., fluorescently labelled ligands and glycoconjugates labelled with a second fluorophore) in communication with (e.g., contacting) glucose. The reactants can be placed in, on, or under the skin. Alternatively, the reactants can be placed within an organ or a vessel (e.g., a vein or artery) in which they are in communication with glucose, which can then be measured by the present method. In the embodiment in which the reactants are positioned in, on or under the skin, glucose is detected by illuminating the skin at the donor excitation wavelength and monitoring the wavelength for the two fluorescent materials. For example, if the fluorescent materials are fluorescein and rhodamine, fluorescence intensities are monitored at 520 nM and 596 nM (i.e., the respective emission maximum wavelengths).

The measure of energy transfer, as detected by a fluorimeter, is then either the ratio of fluorescence intensities at the two emission maximum wavelengths (e.g., FI 520/FI 596) or the quenching of the donor (e.g., fluorescein) fluorescence at its emission maximum as a function of glucose concentration.

A variety of modes of placing the reactants in communication with glucose may be employed in accordance with the principles of the in vivo embodiment of this invention. The reactants can be introduced into the body in any type of supporting or surrounding material which retains the reactants at the desired location and also allows contact or communication with glucose such that it can be measured (i.e., its concentration can be determined by the present method). For example, the reactants may be encapsulated in a microdialysis vessel or in spheres having an inner diameter of about 1 mm and 50–100 μm wall thickness and sealed ends. The encapsulated glucose sensor can be implanted intracutaneously anywhere in the body. In another procedure, reactants may be mixed with silicone or fluorocarbon oils and injected subcutaneously. The reactants may also be tattooed onto the skin or contained in a transcutaneous patch. Alternatively, the reactants may be modified in such a way that when injected subcutaneously, they become bound to cell structure and therefore remain fixed in situ under the skin. For example, RC is known to bind to cells. In addition, the albumin of the FBG complex can be engineered to include a reactive group that binds cells.

In order to determine whether such an in vivo glucometer is feasible, experiments were conducted in which solutions of RC (150 μg/ml) and FBG (2 μg/ml) were injected into mouse skin. Illumination with a laser at the appropriate wavelengths produced strong signals from both the fluorescein and the rhodamine; energy transfer occurred and was detected.

Any in vivo mode of placing the reactants in communication with glucose can be modified to include an insulin pump. The pump could therefore inject insulin into a patient upon detection of inappropriately high glucose levels.

In its broader aspect, the in vitro embodiment of this invention is directed to placing the reactants in communication with a sample of blood or other bodily fluids containing glucose (e.g., urine, extracellular fluid) that has been removed from the body. Glucose is detected and quantified by placing the reactants in communication with the glucose-containing bodily fluid in a fluorimeter.

A variety of modes of placing the reactants in communication with glucose may be employed in accordance with the in vitro embodiment of this invention. For example, the reactants may be adhered to a solid substrate (e.g., a stick) or may be contained in a chamber (e.g., a microdialysis vessel). The reactants may also be contained in a pen cartridge that dispenses an appropriate volume of the reactants into the blood or other bodily substance containing glucose.

The subject invention will now be illustrated by the following examples, which are not to be seen as limiting in any way.

EXAMPLE 1

Preparation of FBG and RC

Fluorescein-BSA-Glucose (FBG) purchased from Sigma and Rhodamine-ConA (RC) purchased from Molecular Probes were dissolved in Hanks Buffered Salt Solution (HBSS) from Gibco to a final concentration of 2 mg/ml. The solutions were then centrifuged at 10,000 g for 30 min. to remove large particulates. The supernatant was then collected and placed on a 10,000 MW Amicon ultrafiltration device and centrifuged at 2,000 g until the ultra-filtrate had passed through the membrane. The retained material was then resuspended in 2 mls. of HBSS and this procedure was repeated until no free fluorescein or rhodamine was detected in the ultra-filtrate.

The final retained material was collected and resuspended in 2 ml. of HBSS and spun one more time at 10,000 g for 30 min. The supernatant was collected and stored at 4° C. until used for energy transfer experiments.

EXAMPLE 2

Determination of the Optimal Concentrations of Fluorescein-BSA-Glucose and Rhodamine-Con A Before competition experiments could be performed with mannose and glucose, optimal concentrations of Fluorescein-BSA-Glucose (FBG) and Rhodamine-Con A (RC) had to be determined. In any solution study using energy transfer, one must avoid the trivial possibility that FRET is occurring simply because the molecules are close enough to one another in solution. Thus, FRET solution studies should ideally be done at concentrations less than 1 mM because at that [] the mol. are separated by 120A units (far enough apart so specifically interact).

Conversely, in these experiments, the concentrations of fluorophore must be high enough to be detected and the concentration of the two species (FBG and RC) must be above their binding constants ($K_bs$).

Initial concentrations of FBG and RC were approximately 2 mg/ml. Maximum transfer occurred when final concentration of FBG was approximately 2 μg/ml and the final concentration of RC was approximately 150 μg/ml. Optimization of FRET was determined by quenching of fluorescein fluorescence, which was 50% maximal at 30 μg/ml RC ([FBG]=2 μg/ml).

EXAMPLE 3

Competition Experiments with Mannose and Glucose

The spectrofluorimeter used for these studies was a Perkin-Elmer MPF-2 equipped with a temperature stage and interfaced to an Apple IIE computer.

Concanavalin A, (con A) is a lectin that specifically binds glucose. A serial dilution of glucose was performed using approximately 2 μg/ml FBG and approximately 150 μg/ml RC from 0–5 mM glucose in HBSS. Various concentrations of glucose were the concentration of glucose increases, the fluorescence intensity at 520 nm increases, and that the ½ maximal response for glucose was approximately 1.8 mg/ml.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method of quantifying glucose in a body fluid sample, comprising the steps of:
   a) contacting the body fluid with a specific binding pair comprising a first member which is a glucose-binding ligand labelled with a first light-absorbing material and a second member which is a glycoconjugate labelled with a second light-absorbing material, the excited state energy level of the first light-absorbing material overlapping with the excited state energy level of the second light-absorbing material, said ligand and said glycoconjugate being chosen such that over the range of physiological concentrations of glucose found in body fluids ranging from 0.05 mg.mL to 5.0 mg/mL they reversibly bind to each other such that glucose present in said body fluid sample can displace said glycoconjugate and reversibly bind to said ligand;

b) determining the extent to which non-radiative fluorescence resonance energy transfer occurs between the first light-absorbing and the second light-absorbing material in the presence of the glycoconjugate displaced by glucose and the ligand reversibly bound to glucose; and c) comparing the result of step (b) with the relationship between the extent of non-radiative energy transfer between the first light-absorbing material and the second light-absorbing material and glucose concentration in the body fluid determined in a calibration step.

2. The method of claim 1 wherein said body fluid sample is chosen from the group consisting of a urine sample and a blood sample.

3. The method of claim 1 wherein at least one member of said specific binding pair is provided on a solid support for use in repeatedly contacting body fluid samples.

4. The method of claim 1 wherein said specific binding pair is provided on a support having a membrane positioned thereon in such a manner that it covers the specific binding pair, said membrane having a pore size which prevents passage of said binding pair from the support to the body fluid but permits passage of glucose between the body fluid and the support.

5. An in vivo method for determining glucose concentration in an individual, comprising the steps of:

a) placing a sensor in communication with glucose present in the body fluids of the individual in such a way that once in place said sensor does not exit the skin of the individual, thereby permitting non-invasive monitoring of the glucose concentration in the body fluids of the individual, said sensor comprising a specific binding pair which comprises a first member which is a glucose-binding ligand labelled with a first light-absorbing material and a second member which is a glycoconjugate labelled with a second light-absorbing material, the excited state energy level of the first light-absorbing material overlapping with the excited state energy level of the second light-absorbing material, said ligand and said glycoconjugate being chosen such that over the range of physiological concentrations of glucose found in body fluids ranging from 0.05 mg/mL to 5.0 mg/mL they reversibly bind to each other such that glucose present in the individual's body fluid can displace said glycoconjugate and reversibly bind to said ligand;

b) non-invasively monitoring the extent to which non-radiative fluorescence energy transfer occurs between the first light-absorbing material and the second light absorbing material in the presence of the glycoconjugate displaced by glucose and the ligand reversibly bound to glucose; and c) comparing the result of step (b) with the relationship between the extent of non-radiative energy transfer and glucose concentration in the individual's body fluids determined in a calibration step.

6. The method of claim 5 wherein said method measures the concentration of glucose in the individual's subcutaneous body fluid, intracutaneous body fluid, or blood.

7. The method of claim 5 wherein said ligand is a glucose-binding lectin.

8. The method of claim 5 wherein said ligand is Concanavalin A.

9. The method of claim 5 wherein the carbohydrate present in said glycoconjugate is capable of binding to glucose-binding ligands.

10. The method of claim 1 or claim 5 wherein said glycoconjugate is chosen from the group consisting of glycosylated serum albumin capable of binding to glucose-binding ligands and glycosylated bovine serum albumin capable of binding to glucose-binding ligands.

11. The method of claim 5 wherein said first and second light-absorbing materials are fluorophores.

12. The method of claim 11 wherein at least one of fluorophores is chosen from the group consisting of fluorescein and rhodamine.

13. The method of claim 5 wherein said ligand is labelled with a fluorophore which is the donor and said glycoconjugate is labelled with a fluorophore which is the acceptor in the non-radiative fluorescence resonance energy transfer process.

14. The method of claim 5 wherein said ligand is labelled with a fluorophore which is the acceptor and said glycoconjugate is labelled with a fluorophore which is the donor in the non-radiative fluorescence resonance energy transfer process.

15. The method of claim 5 wherein the non-radiative fluorescence resonance energy transfer is determined by measuring the ratio of the light emissions attributable to the first and second light absorbing molecules.

16. The method of claim 5 wherein the first member of the specific binding pair is rhodamine-labelled Concanavalin A, the second member of the specific binding pair is fluorescence-labelled glycosylated serum albumin capable of binding to glucose-binding ligands, and the non-radiative fluorescence resonance energy transfer is determined by measuring the ratio of the light emissions attributable to rhodamine and fluorescein.

17. The method of claim 5 wherein said sensor is placed on, in, or under the skin of the individual.

18. The method of claim 5 wherein said specific binding pair is placed in a microdialysis vessel and then subcutaneously implanted in the individual.

19. The method of claim 5 wherein said specific binding pair is encapsulated and then subcutaneously implanted in the individual.

20. The method of claim 5 wherein said specific binding pair is mixed with an oil into which glucose can pass and then injected subcutaneously in the individual.

21. The method of claim 5 wherein said specific binding pair is tatooed into the skin of the individual.

22. The method of claim 5 wherein the components of said specific binding pair are chemically modified to enable them to bind to the cells of the individual.

23. The method of claim 5 wherein said specific binding pair is bound to a solid support which is then implanted in the individual, said support retaining said specific binding pair at the desired location once implanted in the individual.

24. The method of claim 5 wherein said said specific binding pair is illuminated, and said energy transfer is monitored, through the skin of the individual.

25. The method of claim 5 wherein the non-radiative fluorescence resonance energy transfer is determined by assessing whether there is a decrease in donor lifetime, a quenching of donor fluorescence, an enhancement of acceptor fluorescence intensity or a depolarization of fluorescence relative to excitation, alone or in combination.

26. A sensor for non-invasively monitoring glucose concentration in an individual comprising a specific binding pair which comprises a first member which is a glucose-binding ligand labelled with a first light-absorbing material and a second member which is a glycoconjugate labelled with a second light-absorbing material, the excited state energy level of the first light-absorbing material overlapping with the excited state energy level of the second light-absorbing material, said ligand and said glycoconjugate being chosen such that they reversibly bind to each other over the physiological range of glucose concentrations found in the body fluid of the individual ranging from 0.05 mg/mL to 5.0 mg/mL to enable glucose present in the individual's body fluid to displace said glycoconjugate and reversibly bind to said ligand, the components of said sensor being configured such that once implanted in the individual said sensor does not exit the skin of the individual, thereby permitting non-invasive monitoring of the glucose concentration in the body fluids of the individual in the presence of the glycoconjugate displaced by glucose and the ligand reversibly bound to glucose.

27. The sensor of claim 26 wherein said first member of said specific binding pair is a fluorescently-labelled lectin and said second member of said specific binding pair is a fluorescently-labelled blycoconjugate.

28. The sensor of claim 26 wherein said first member of said specific binding pair is rhodamine-labelled Concanavalin A and said second member of said specific binding pair is fluorescein-labelled glycosylated serum albumin capable of binding to glucose-binding ligands.

* * * * *